United States Patent [19]

Dinius et al.

[11] 4,451,254
[45] May 29, 1984

[54] IMPLANT SYSTEM

[75] Inventors: Harold B. Dinius; John R. Huizenga, both of Mooresville, Ind.

[73] Assignee: Eli Lilly and Company, Indianapolis, Ind.

[21] Appl. No.: 358,459

[22] Filed: Mar. 15, 1982

[51] Int. Cl.³ .............................................. A61M 5/18
[52] U.S. Cl. ...................................... 604/62; 206/535; 221/198; 221/232; 221/279
[58] Field of Search .................................. 604/60–64, 604/241; 221/198, 232, 279; 206/535, 536

[56] References Cited

U.S. PATENT DOCUMENTS

| | | | |
|---|---|---|---|
| 1,262,732 | 4/1918 | Andrews | 604/62 |
| 1,601,932 | 10/1926 | Viol | 604/64 |
| 2,269,963 | 1/1942 | Wappler | 128/217 |
| 2,513,014 | 6/1959 | Fields | 128/217 |
| 2,577,556 | 12/1951 | Williams | 604/241 |
| 2,601,852 | 7/1952 | Wendt | 128/264 |
| 2,620,796 | 12/1952 | Eriksen et al. | 604/62 |
| 2,625,927 | 1/1953 | Rosenbloom | 124/27 |
| 2,632,444 | 3/1953 | Kas | 128/217 |
| 2,634,726 | 4/1953 | Hanson | 128/221 |
| 2,638,897 | 5/1953 | Poitras | 128/221 |
| 2,659,369 | 11/1953 | Lipman | 128/217 |
| 2,718,299 | 9/1955 | Atwater et al. | 206/42 |
| 2,751,907 | 6/1956 | Hickey | 128/221 |
| 2,761,446 | 9/1956 | Reed | 128/217 |
| 2,850,013 | 9/1958 | Cordis | 128/217 |
| 2,883,984 | 4/1959 | Candido, Jr. | 128/217 |
| 2,907,327 | 10/1959 | White | 128/217 |
| 3,016,895 | 1/1962 | Sein | 128/217 |
| 3,025,953 | 3/1962 | Taggart et al. | 206/535 |
| 3,088,207 | 5/1963 | Borsuk | 32/60 |
| 3,128,744 | 4/1964 | Jefferts et al. | 119/3 |
| 3,402,712 | 9/1968 | Eisenhand | 128/217 |
| 3,520,299 | 7/1970 | Lott | 128/217 |
| 3,620,216 | 11/1971 | Szymanski | 128/217 |
| 3,669,104 | 6/1972 | Wyatt | 128/217 |
| 3,774,607 | 11/1973 | Schmitz | 128/217 |
| 4,060,083 | 11/1977 | Hanson | 128/217 |
| 4,077,406 | 3/1978 | Sandhage | 128/217 |
| 4,086,914 | 5/1978 | Moore | 128/217 |

FOREIGN PATENT DOCUMENTS 806702  6/1951  Fed. Rep. of Germany ........ 604/60

Primary Examiner—Dalton L. Truluck
Attorney, Agent, or Firm—Barnes & Thornburg

[57] ABSTRACT

Implants may be placed in animals in the field with a system including an implanter and cartridge-like container for a plurality of implants. The cartridge is transparent and encloses a plurality of enlongated implants arranged side-to-side, transverse to the central axis of the cartridge. The implants may be moved manually along the central axis of the cartridge toward one end and stopped in alignment parallel with the end of the cartridge and with one implant aligned with a pair of openings in the cartridge, one at each end of the implant. The implanter carries a sharpened tubular needle and a plunger, slidable along an axis aligned with the central axis of the tubular needle. The implanter has an opening into which the cartridge may be fitted and retained. The implanter and cartridge have interfitting surfaces to position the cartridge with its pair of openings lying upon the central axis of the hollow needle and to retain the cartridge in the implanter so that the plunger may be passed repeatedly through the pair of openings in the cartridge and move the implants, one after the other, through the sharpened tubular needle into the animals. The implants are protected from contamination until implantation.

12 Claims, 3 Drawing Figures

IMPLANT SYSTEM

This invention relates to a new multi-dose system to insert an implant into an animal from a clean container.

Implants have been developed to introduce therapeutic agents into the body of an animal for providing uniform release of drugs over long periods of time. Such implants may comprise a drug carrier formed of polyorganopolysiloxane rubber composition (more generally known as silicone rubber) which is non-reactive toward the drug, non-toxic to the body, and known to be compatible with living tissue even after a prolonged implantation. The drugs are in a powder or semi-solid or liquid form, and generally have appreciable solubility in the polymer composition of the organopolysiloxane rubber composition. Such drugs are introduced from the carrier into the body of the animal by diffusion or migration interstitially between the elastomer molecules to the outer surface of the carrier, from which they are removed by the animal's body fluids. The term "drug" is used in its broad sense as synonomous with therapeutic agents, medicaments, and the like, as intended to include hormones, vitamins, antibiotics, anticoagulants, cancericidal agents, spermicidal agents, vasoactive agents, and other medicinals and medications effective to treat undesirable conditions existing in or on an animal body or in an animal's body fluids.

Such implants are not eroded by the animal's body fluids and permit the exposure of the animal to the effect of the drug to be terminated at will by removal of the implant. With termination of exposure of the animal to the effects of the drug thus controllable, a livestock owner has the ability to more rapidly meet the demands of the marketplace by electing to shorten the time between treatment of the animal with a drug, such as a growth stimulant, and slaughtering of the animal for use.

To provide treatment of animals, for example with estradial, and permit termination of such treatment, implants in cylindrical form having lengths on the order of an inch or more and diameters of a significant fraction of an inch are used. The insertion of such implants into the animal's body must frequently take place at a remote site, such as at a livestock ranch or at feeder lots in the field. Furthermore, the insertion of such implants must be performed by ranch and field hands frequently under dirty conditions.

This invention permits the handling of implants at such remote sites without their contamination. In this invention, a plurality of such implants are contained in a transparent and clean enclosure, and the implants are placed in the animal with an implanter and a sharpened hollow tube. The container has a pair of aligned openings at one end, and the implanter and container have interfitting surfaces adapted to permit the container to be positioned and retained on the implanter. The plurality of implants may be moved one-by-one and stopped in alignment parallel with the end of the package and with the pair of openings. When the cartridge is in position on the implanter, its pair of openings lies in alignment with the central axis of the hollow needle of the implanter. A plunger is carried within the implanter and is slidable along an axis aligned with the central axis of the sharpened hollow tube. The plunger may slide through the container openings, engage an implant, and move the implant through the sharpened hollow tube into the animal. The implants may be moved, one after the other, along the central axis of the container, permitting the system to repeatedly place the plurality of implants, one after another, into animals.

The implanter of the system includes a body having a forward portion and a rear portion forming a central bore. The implanter body also forms an elongated slot between the outer surface of the body and the central bore and a rectangular opening adjacent the forward portion of the body. The rectangular opening has its central axis transverse to the axes of the elongated slot and central bore. The forward portion of the implanter body is adapted to accept and engage a sharpened hollow tube and to position its bore in alignment with the axis of the central bore of the implanter body. The plunger that is slidably carried in the central bore of the body includes an elongated rod and a web extending transversely through the elongated slot. A surface adapted for engagement by the thumb or fingers of an operator extends transversely from the web outside the implanter body to permit the plunger to be operated. When the plunger is operated, the central bore guides the forward end of the elongated rod through the bore of the hollow tube. In its rearward position, the forward end of the elongated rod lies rearwardly of the rectangular opening of the implanter body.

The implant enclosure, or container, comprises a cartridge for use with the implanter. The cartridge includes a tray-like portion and a slotted top with an implant pusher between the tray-like portion and the top. The pusher has an outwardly projecting tab, extending through the slot in the top to permit the user to move the pusher manually. The pusher conveniently includes a surface forming a pointer, and the cartridge includes a sequence of numbers related to the number of implants within the cartridge. The tray-like portion of the cartridge forms two sides having aligned openings larger than the cross-sectional area of the implants that it contains. The cartridge and the contained pusher may be adapted to preclude the advancement and retraction of the pusher and to retain the pusher against movement by gravity in order that the implants may be retained in their parallel side-by-side arrangement. One manner of accomplishing this is to provide the tray-like portion with a plurality of detents spaced equally in a row a distance equal to the thickness of an implant and providing the implant pusher with ratchet teeth to engage the detents.

For use in the field, it is desirable that the implant plunger be retained rearwardly within the implanter so that its forwardmost end is rearward of the rectangular opening into which the cartridge fits. The cartridge and implants are thus free of interference as they are placed within the implanter.

In addition, it is advisable to signal the user when the implant is about to be expelled from the forward end of the sharpened hollow tube into the animal. In use, the sharpened tube will be inserted into and embedded in the animal's body, preferably the animal's ear, and being unable to see the tube opening, the user will want to know when the implant is leaving the forward end of the hollow tube. Users frequently want to withdraw the implanter as the implant is being pushed from its interior. It is also advisable to retain the movement of the plunger in a position where the implant is not yet exposed at the forward portion of the hollow tube to prevent the implant from being exposed, or expelled accidentally from the implanter.

The implanter, at its central slot and at the web of the plunger, is preferably provided with interengaging sufaces adjacent the rear of the central slot to retain the plunger with its forward end lying rearwardly of the rectangular opening in the implanter. In addition, such interengaging surfaces may be provided at a mid-point in the central slot, positioned to impede the travel of the plunger and to hold the plunger in position with the forward portion of its elongated rod within and spaced rearwardly from the forward end of the hollow tube a distance about equal to the length of an implant.

Using the system of this invention, a plurality of implants can be provided within a closed container that can be maintained free of contaminants and transported to a remote site for use. At such a site, the container can be opened and placed in position on the implanter so that the implants within the container are protected from dirt and contamination at the site. With the container in position on the implants, the implants can be placed one after another into a plurality of animals. Such a system and method are capable of maintaining the implant in a clean condition during its transportation and handling, and permitting the implant to be placed in an animal without contamination in handling.

The implanter is lightweight and easy to use. Its features permit the straight-line application of force with one hand in a straight line along the axis of the implanter. The container, with its plurality of doses, permits the treatment of a plurality of animals without extensive container handling and at a reasonable cost per dose. The containers are small and are sealed against contamination, and a number of containers may be easily carried by users to the remote site of use.

Other features and advantages of this invention will be apparent from the following specification and from the drawings in which.

Figure 1:
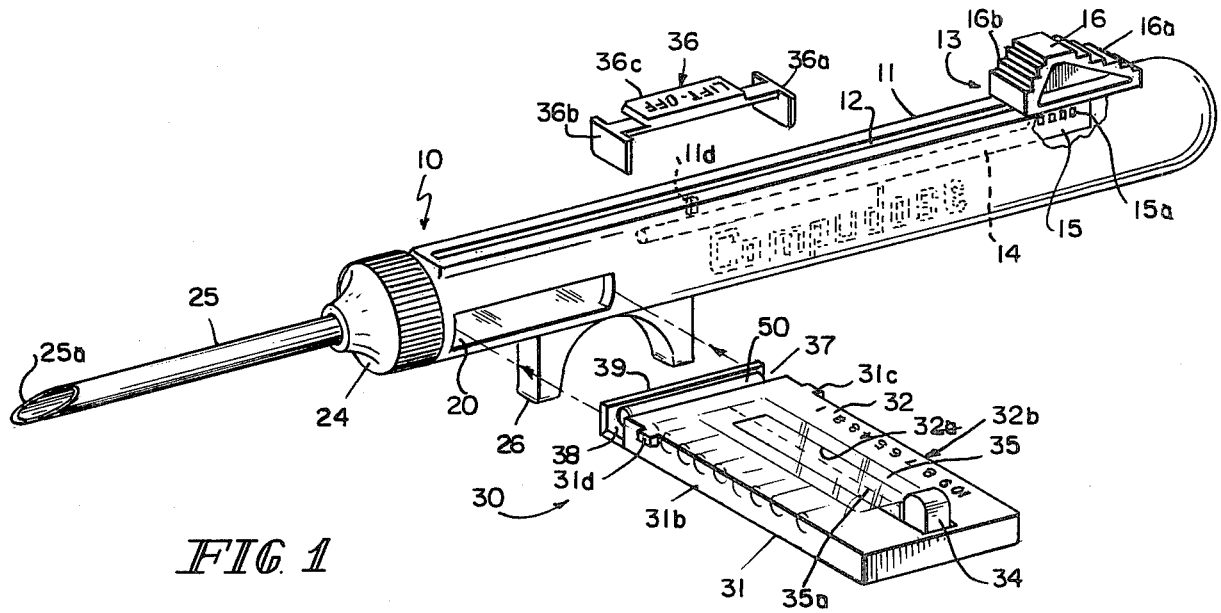
FIG. 1 is a perspective view of the system of the invention showing an implanter and a cartridge of the invention.

FIG. 1 shows in perspective view the system of this invention. The system includes an implanter 10 and an implant container 30. The container 30 provides means to enclose transparently a plurality of elongated implants 50 arranged side-by-side transverse to the central axis of the container. The implanter provides means to carry a sharpened tubular needle 25 and a plunger 13 slidable within the implanter along an axis aligned with the central axis of the tubular needle. These two means, the implanter 10 and the container 30, have interfitting surfaces permitting the container 30 to be inserted into and positioned in the implanter 10 so that the plunger may move implants, one after the other, from the container 30 through the sharpened tubular needle 25 into an animal.

This multi-dose system can be comprised of but a few parts and is operated manually to provide a simple and reliable system for the treatment of animals. Although the preferred system is particularly adapted for containers of ten implants, the system may be adapted for larger or smaller doses. The preferred ten-dose system is a convenient and practical size. The container is small enough that a number of such containers can be easily carried by users in the field. Its features preclude contamination of the implants in use, and it can be used without the inconvenience of frequent reloading, and at a reasonable cost per dose. The system includes a number of other features that make it reliable and conveniently usable in the field.

Figure 2:
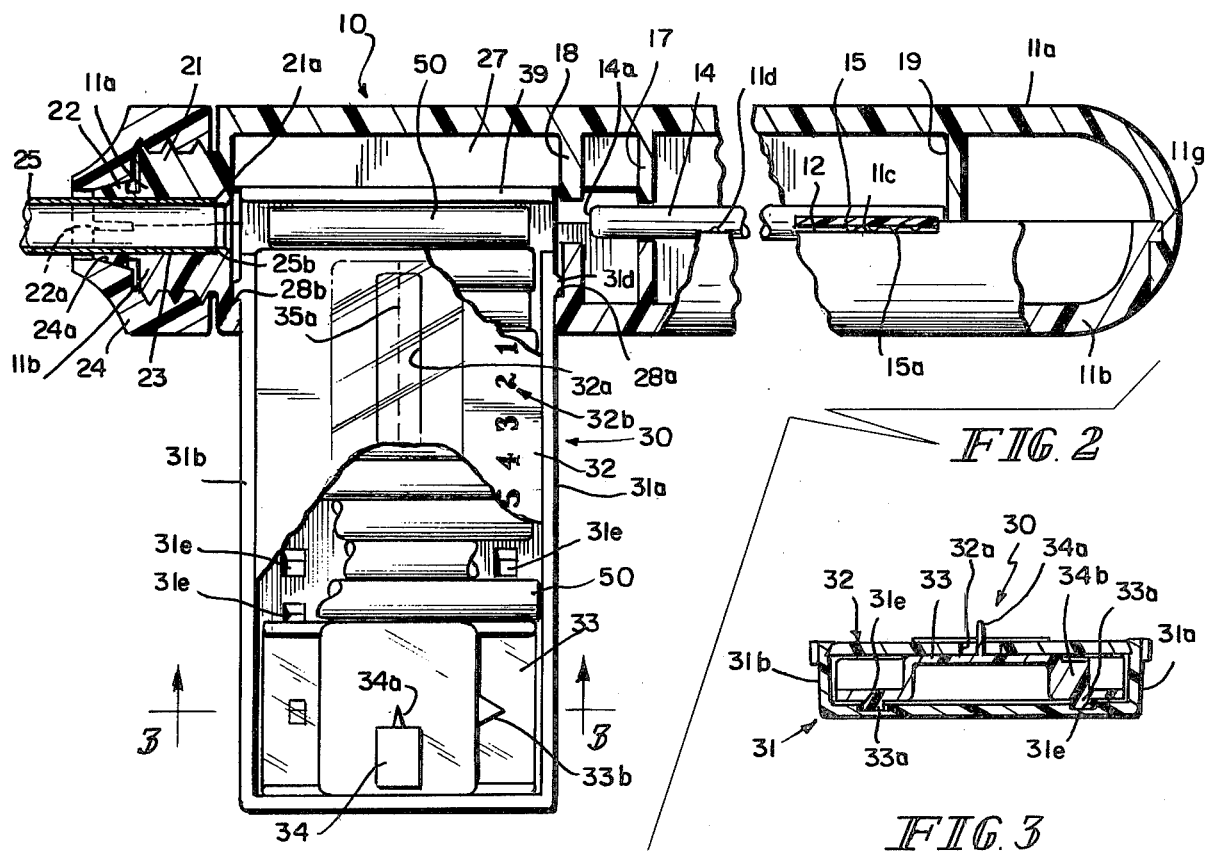
FIG. 2 is a fragmentary view, broken away to show in cross section the interior structure of the implanter and the cartridge and their engagement when the cartridge is in place on the implanter.

The implanter 10 includes but a few parts. The implanter includes an elongated body 11 which is conveniently molded from impact-resistant thermoplastic materials, ABS being the currently preferred such material. The body 11 may be molded in two sections, one on either side of a cross section through an elongated central slot 12. The two body sections 11a and 11b may be substantially hollow, as shown in FIG. 2, having molded therein such strengthening partitions and sections (such as 17, 18, and 19, FIG. 2) as may be advisable. A plunger 13 is slidably carried within the body 11. The plunger includes an elongated rod 14, a web 15 extending transversely from the rod through the central slot 12 of the implanter body, and a thumb button 16, having serrated surfaces 16a and 16b that extend transversely from the web 15 outside of the implanter body 11. The plunger 13 is slidably carried within the implanter body 11. The plunger 13 is guided within the body 11 by the slot 12 and body portions such as the projecting partitions 17, 18, and 19 (shown in FIG. 2) within the body 11. The two body sections 11a and 11b and their internal partitions (e.g., 17, 18, and 19) thus define a central bore for the plunger.

In its normal position, the plunger 13 is retained adjacent the rear portion of the implanter 10 as shown in FIG. 1. The plunger is held in the position shown in FIG. 1 by interengaging surfaces of the plunger and the implanter body. In the preferred embodiment, the web 15 of the plunger is provided with a plurality of ratchet teeth 15a as shown in FIGS. 1 and 2. The section 11b of the implanter body includes a pair of projecting tabs 11c and 11d, shown in FIGS. 1 and 2. As shown in FIG. 2, the ratchet teeth 15a and the tab 11c within the central slot 12 of the implanter body interfit to impede the travel of the plunger forwardly within the implanter. The plunger, like the sections of the implanter body, is molded from a thermoplastic material, preferably ABS. The dimensions of the web 15, the ratchet teeth 15a, the tab 11c, and the width of the central slot 12 are such that the plunger may be forced forwardly so that the ratchet teeth 15a are disengaged from tab 11c, permitting the plunger to slide forwardly within the implanter until it reaches tab 11d, whose purpose will be explained below.

The forward end of the implanter is provided with a rectangular opening 20 into which the cartridge 30 may be fitted. Adjacent the rectangular opening 20 at the forward portion of the implanter body is a projecting threaded portion 21 (shown in FIG. 2), and immediately forward of the threaded portion 21 is a tapered conical portion 22 with a split or gap 22a. The split, conical, and threaded portions (21 and 22) surround coaxially a central bore 23 at the forward portion of the body, all as shown in FIG. 2. The forward portion of the implanter body can thus be adapted to accept and engage a hollow tube and to position its bore in alignment with the axis of the central bore of the implanter body on which the plunger 13 moves.

A hollow tube 25 with a sharpened forward end 25a and a blunt rear end 25b (shown in FIG. 2) may be securely fastened to the forward end of the implanter body. The hollow tube 25 is inserted into the central bore 23 at the forward portion of the implanter body until it seats upon a boss 21a. The implanter includes a threaded cap 24 having an inner conical surface 24a adapted to mate the split, conical surface 22 at the forward end of the implanter body. As the cap 24 is tightened onto the threaded portion 21, its inner conical surface 24a compresses the split conical surface 22 and its split portion 22a onto the outer surface of the hollow needle 25 securely fixing the hollow needle to the implanter body. This arrangement permits the hollow tube to be rotated about the central axis of the implanter body to position its sharpened forward end 25a at any convenient angle for use by loosening the threaded cap 24, adjusting the position of the sharpened end 25a, and retightening the threaded cap 24.

The implanter body has an outside diameter on the order of one inch. Immediately beneath the central slot along which the thumb button 16 is pushed, the implanter body 11 may be provided with a finger grip 26, and its outer surface may be provided with a raised logo trademark to permit it to be firmly gripped in use.

The portion of the implanter body 11 defining the rectangular opening 20 forms a cartridge slot and chamber as shown in FIG. 2. When the cartridge 30 is inserted into the rectangular opening 20, as shown in FIG. 1, it becomes locked in position in the implanter as shown in FIG. 2. The implanter can include a molded-in projection 27 to stop and position the cartridge 30 within the implanter body 11. The implanter body may also be formed to provide detents 28a and 28b within the implanter body 11 adjacent the sides of the rectangular opening 20. The detents may be engaged by projecting tabs at the sides of the container 30 to retain the container securely within the implanter during use. Although two detented surfaces 28a and 28b are shown in FIG. 2, only one such detent may be necessary. The surfaces within the implanter body 10 accessible through the rectangular opening 20 thus define a chamber into which the cartridge-like container 30 may be interfitted and positioned and retained for use.

The implants 50 are long and cylindrical in shape, as shown in FIGS. 1 and 2. The container 30 comprises in essence a transparent rectangular tube enclosing the implants and in which the implants 50 are arranged parallel and side by side with their long axis lying transverse to the central axis of the catridge 30 as shown in FIG. 2.

The cartridge 30 includes a tray-like portion 31, a slotted top 32, and a pusher 33 having a projecting button 34. The slot in top 32 is covered with a slot tape 35 having a weakened tear line 35a along the central axis of the slot 32a. The slot tape 35 prevents contaminants from entering the package 30 through the slot 32. The forward portion of the cartridge is provided with a lift-off tab 36 which is fastened to the top 32 at the end opposite the slot through which button 34 projects. The lift-off tab includes two downwardly projecting panels 36a and 36b and a finger tab 36c. The lift-off tab 36 is fastened to top 32 at a weakened score line so that by engaging lift-off tab 36 and folding it backwardly, it may be disengaged from the cartridge 30 to provide access to the implants 50 carried within the cartridge.

Figure 3:
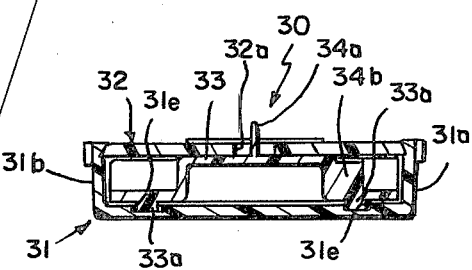
FIG. 3 is a cross-sectional view taken along lines 3—3 of FIG. 2.

As shown in FIGS. 1-3, the tray-like portion 31 forms two sides 31a and 31b that form a pair of aligned openings 37 and 38 adjacent the end of the cartridge. As shown in FIG. 2, the plurality of implants may be moved by the pusher 33 along its central axis toward end 39 where they are stopped one-by-one in alignment parallel to cartridge end 39 and the pair of openings 37 and 38.

When cartridge end 39 of the cartridge 30 is inserted into the rectangular opening 20, it is stopped by the wall 27 within the implanter body, positioning the cartridge 30 so that the implants 50 may be presented one-by-one within the implanter, aligned as shown in FIG. 2 between the forward end of the plunger 14a and the bore of the hollow tube 25. The sides 31a and 31b of the cartridge may be provided with tabs 31c and 31d that snap into the detents 28a and 28b of the implanter body and retain the cartridge 30 within the implanter body.

The pusher 33 may fit within the cartridge 30 in such a manner that its movement is impeded by the interengagement of its outer surface with the inner surface of the cartridge. The cartridge 30 may be provided with means providing for the advancement of the implants toward the openings 37 and 38 one-by-one. Such means can impede the advancement and retraction of the pusher 33 within the cartridge and can include, as shown in FIGS. 2 and 3, a plurality of detents 31e in the tray-like portion 31 spaced equally in a row a distance equal to the thickness of an implant. The pusher 33 may be provided with ratchet surfaces 33a to engage the detents 31e, thereby allowing the pusher 33 to be advanced toward end 39 step-by-step in increments of movement equal to the thickness of an implant. Pusher 33 at its button 34 may be provided with a sharpened extending tab 34a to permit it to more easily separate the slot tape 35 at its score line 35a as the pusher 33 is advanced toward end 39.

The pusher 33 also includes a portion defining a pointer 33b which cooperates with a series of numbers 32b, shown in FIGS. 1 and 2, embossed in the cartridge top 32. As the pusher 33 is moved forward by button 34, pointer 33b points to the number 32b in the top 32 that represents the number of implants remaining within the package 30.

When this system is used in the field, the user has only to remove one of the cartridges from his pocket, tear off the lift tab 36, and insert the cartridge 30 into the rectangular opening 20 in the implanter 10. If the sharpened end 25a of hollow tube 25 is not at the right angle, it may be easily adjusted by simply loosening the threaded cap 24 and rotating tube 25 to the desired orientation. The farm animal will probably be captured within the squeeze chute. The user has merely to grasp the animal's ear with one hand, folding it gently so that he may insert the sharpened end 25a of the implanter into the animal's ear. By pressure on the thumb button 16, he may slide the plunger forwardly within the implanter body, and as he does so, the forward end 14a of the plunger passes through opening 37 of the cartridge 30 and engages the end of an implant 50, pushing it from within the cartridge 30, through opening 38, and into the hollow bore of sharpened tube 25. As the forward end of the implant 50 nears the sharpened end 25a of the hollow tube 25, the ratchet 15a on the web of the plunger 13 interengages tab 11d, which is shown in FIG. 1 as at a mid-point of the central slot 12. Interengagement of the ratchets 15a and tab 11d at the central slot 12 of the implanter signal the user that the implant is about to be expelled from the forward end of the implanter into the animal. The interengagement also will hold the plunger 13 in this position. When the user is ready to insert the implant into the animal, he has only to again push forwardly on the plunger 13, thereby pushing the implant 15 forwardly and out of the sharpened end 25a of the hollow tube 25 and into the animal.

The implanter body may conveniently have a length on the order of eight inches and a diameter of one inch. It may be conveniently molded in two sections. The walls of the sections can have generally a thickness on the order of one-tenth of an inch. The internal partitions, such as partitions 17, 18, 19, and 27, may have a thickness on the order of half the outer shell, or about 0.050 inch. Split conical portion 22 at the forward portion of the implanter body may have a length of about ¼ of an inch, and the threaded portion 21 may have a length on the order of ⅜ of an inch. The body parts may be molded with the draft on the order of 2° and have minimum fillets and radii on the order of 0.010 to 0.015 inch. The two sections may be held together with assembly tabs as shown, for example, by 11g of FIG. 2. Similar interengaging assembly tabs can be provided along the length of body parts 11a and 11b at their bottoms. Of course, threaded cap 24 will retain the parts 11a and 11b as an integral unit when threaded in place.

The cartridge 30 may be molded from clear polyvinyl chloride in two pieces. The tray-like bottom portion 31 may be molded in one piece, and the top 32 with the lift-off tab 36 may be molded as another piece. The dimensions of the typical cartridge are approximately 1⅜ inches in width and 2¾ inches in length. The thickness, top to bottom, of the cartridge can be less than ⅜ of an inch. The pusher 33 within such a cartridge will fit from side-to-side within the tray-like bottom portion 31. Its length along the central axis of the cartridge can be typically ¾ of an inch and the button 34 can project upwardly, for example, about ¼ of an inch beyond the top 32 of the cartridge. These dimensions are for the preferred cartridge containing ten implants. The top and the bottom of the cartridge typically have uniform thicknesses, for example, on the order of 0.050 inch.

The specific embodiment of the invention shown and described above is capable of modification without departure from the scope of the following claims.

What is claimed is:

1. Apparatus for inserting elongated cylindrical implants in animals, comprising an elongated implanter body having forward and rearward portions and defining a central bore, an elongated slot between such bore and an outer surface of the body and a transverse cartridge-receiving opening in the forward portion of the body and intersecting such bore, an implant tube having a sharpened forward end and means to mount such tube to the forward end of the body in alignment with said central bore, a plunger including an elongated rod slidable in the central bore between a rearward position in which its forward end is behind the cartridge-receiving opening and a forward position in which it extends into the implant tube to expel an implant therefrom, said plunger having a web extending through said slot and supporting a thumb-engageable surface outside said body for engagement by the thumb of an operator for moving the plunger between its two positions, a cartridge removably mounted in said cartridge-receiving opening and containing a plurality of implants in side-by-side relationship and parallel to said central bore, and means for moving said implants successively into alignment with said central bore of the body for movement by the plunger forwardly through the implant tube, means adjacent the rear of the slot for engaging said web to retain the plunger in a retracted position behind an implant moved from said cartridge into alignment with said bore, one of said implanter body and said plunger web having a laterally extending tooth surface thereon and the other having a tooth-engaging surface thereon to interengage such tooth surface intermediate the travel of the plunger to impede the movement of the plunger at an intermediate position in which its forward end lies within the implant tube and spaced rearward of its sharpened forward end a distance approximately equal to the length of an implant so as to position an implant substantially at such forward end of the tube for delivery therefrom, said interengaging tooth and tooth-engaging surfaces being disengageable and said plunger being movable beyond said intermediate point by thumb pressure on said thumb-engageable surface to expel such implant from the tube into an animal when the tube has been inserted through the skin of the animal.

2. Apparatus as in claim 1, wherein said cartridge includes a row of detents spaced equally by a distance equal to the thickness of an implant, and said cartridge has an implant pusher for advancing the implants therein to the central bore and such pusher includes a ratchet tooth to engage the detents and impede the movement of the implant pusher at intervals equal to the thickness of an implant and to retain the implant pusher against movement by gravity.

3. Apparatus for inserting elongated cylindrical implants in animals, comprising an implanter body having forward and rearward portions and forming a central bore, an elongated central slot between such bore and an outer surface of the body, and a lateral cartridge-receiving opening in the forward portion of the body and intersecting such bore, an implant tube having a sharpened forward end and means to mount such tube in the forward end of the body in alignment with said central bore, a plunger including an elongated rod slidable in the central bore between a rearward position in which its forward end is behind the cartridge-receiving opening and a forward position in which it extends into the implant tube to expel an implant therefrom, said plunger having a web extending through said slot and supporting a surface outside said body for engagement by the thumb of an operator for moving the plunger between its two positions, a cartridge removably mounted in said cartridge-receiving opening and containing a plurality of implants in side-by-side relationship and parallel to said cental bore, and means for moving said implants successively into alignment with said central bore of the body for movement by the plunger forwardly through the implant tube, the implanter body including tabs extending into the central slot adjacent its rear and its mid-point, and said plunger web including ratchet teeth as surfaces to interengage said tabs and impede the travel of and hold the plunger, said rear tabs retaining the plunger in a retracted position behind an implant moved into alignment with said bore, and said mid-point tabs being operative to impede the movement of the plunger at an intermediate position in which its forward end lies within the implant tube and spaced rearward of its sharpened forward end a distance approximately equal to the length of an implant so as to position an implant substantially at such forward end of the tube for delivery therefrom, said plunger being movable beyond said intermediate point by thumb pressure on said surface to expel such implant from the tube into an animal when the tube has been inserted through the skin of the animal, and wherein:

the cartridge includes a plurality of detents spaced equally in a row a distance equal to the thickness of an implant, and said cartridge has an implant pusher for advancing the implants therein to the central bore and such pusher includes ratchet teeth to engage the detents and impede the advancement and retraction of the implant pusher at intervals of movement equal to the thickness of an implant and to retain the implant pusher against movement by gravity, the forward and rearward sides of said cartridge have openings aligned with the central bore and each such side includes a projecting tab adjacent the aligned openings, and the implanter body includes a detent at each side of the cartridge-receiving opening into which the projecting side tabs of the cartridge extend when the cartridge is in position in the implanter body, and the implanter body has a boss opposite such opening upon which said one end of the cartridge seats when in position in the implanter body.

4. Apparatus for inserting an implant into an animal, comprising:

an implanter body having a forward portion and a rearward portion and forming a central bore, an elongated slot between an outer surface of the body and the central bore, a transverse rectangular opening in the forward portion of the body between the central bore and the outer surface of the body, a tube having a sharpened forward end and means to mount such tube in the forward end of the body in alignment with the central bore of the implanter body, and a plunger, including an elongated rod and a transversely extending web, slidably carried in the implanter body, the forward end of the elongated rod extending through the hollow tube and its forward end when the plunger slides forwardly within the implanter body, a cartridge containing a plurality of implants and fitted within the rectangular opening of the implanter body, said cartridge including a rectangular tray-like portion and a slotted top and an implant pusher between the tray-like portion and top with an outwardly projecting button extending through the slotted top to permit movement of the pusher, said pusher including a pointer, and said cartridge including a sequence of numbers related to the number of implants within the cartridge, the tray-like portion forming two sides having aligned openings larger than the cross-sectional area of the implants, and wherein the implanter body includes tabs extending into the central slot adjacent its rear and its mid-point and said plunger web includes ratchet teeth as surfaces to engage said tabs and impede the travel of, and hold, the plunger, the cartridge tray-like portion includes a plurality of detents spaced equally in a row a distance equal to the thickness of an implant, and said implant pusher includes a ratchet tooth to engage the detents and impede the advancement and retraction of the implant pusher at intervals of movement equal to the thickness of an implant and to retain the implant pusher against movement by gravity, the sides of said cartridge tray-like portion each include a projecting tab adjacent the aligned openings and the implanter body includes a detent at each side of the rectangular opening into which the projecting side tabs of the cartridge extend when the cartridge is in position in the implanter body, and the implanter body has a boss opposite its rectangular opening upon which the end of the cartridge seats when in position in the implanter body.

5. An implanter, comprising a body having a forward portion and a rearward portion and forming a central bore, an elongated slot between an outer surface of the body and the central bore, a transverse rectangular opening adjacent the forward portion of the body between the central bore and the outer surface of the body, a tube having a sharpened end and means to mount such tube at the forward end of the body in alignment with its central bore, a cartridge removably mounted in said transverse opening and containing a plurality of rod-like implants, and means for moving said implants successively into said bore from movement through said tube, a plunger, including an elongated rod slidably carried in the central bore of the implanter body and a web on said rod extending through said elongated slot and having a thumb-engageable surface outside of the implanter body, the central bore guiding the forward end of the elongated rod along an axis through said sharpened tube when the plunger slides forwardly within the implanter body, the forward end of the elongated rod lying rearwardly of the rectangular opening of the implanter body when the plunger slides rearwardly within the implanter body, said plunger web having laterally extending engagement surfaces thereon, and the implanter body having surfaces at the side of and adjacent the rear of its elongated slot for engaging said web surfaces to retain the plunger with the forward end of its rod lying rearwardly of the rectangular opening and having surfaces at a mid-point of its elongated slot for engaging said web surfaces to impede the travel of the plunger and hold the plunger with the forward portion of the elongated rod within and spaced rearwardly of the forward end of the hollow tube a distance about equal to the length of the implant.

6. An implant container, comprising:

a cartridge containing a plurality of implants, said cartridge including a rectangular tray-like portion and a slotted top and an implant pusher between the tray-like portion and top with an outwardly projecting button extending through the slotted top to permit movement of the pusher, the cartridge tray-like portion including a plurality of detents spaced equally in a row a distance equal to the thickness of an implant, and the implant pusher including ratchet teeth to engage the detents and impede the advancement and retraction of the implant pusher at intervals of movement equal to the thickness of an implant and to retain the implant pusher against movement by gravity, said pusher including a pointer and said cartridge including a sequence of numbers related to the number of implants within the cartridge, the tray-like portion forming two sides having aligned openings larger than the cross-sectional area of the implants, the sides of said cartridge tray-like portion each including a projecting tab adjacent the aligned openings.

7. A container for implants, comprising:

a cartridge containing a plurality of implants, said cartridge including a rectangular tray-like portion and a slotted top and an implant pusher between the tray-like portion and top with an outwardly projecting button extending through the slotted top to permit movement of the pusher, said pusher including a surface forming a pointer and said cartridge including a sequence of numbers related to the number of implants within the cartridge, the tray-like portion forming two sides having aligned openings larger than the cross-sectional area of the implants, a tape covering the slot through which the projecting portion of the pusher moves, and means on the pusher for splitting said tape as the pusher is moved to push the implants.

8. The container of claim 7 wherein said cartridge has an end wall against which the implants move as they are advanced by the plunger, and said openings are positioned to be in alignment with an implant lying against such wall, with the addition of break-away tab means normally closing said aligned side openings but manually removable to expose the openings for movement of the implants from the cartridges.

9. A container for implants, comprising:

a cartridge containing a plurality of implants, said cartridge including a rectangular tray-like portion and a slotted top and an inplant pusher between the tray-like portion and top with an outwardly projecting button extending through the slotted top to permit movement of the pusher, said pusher including a surface forming a pointer and said cartridge including a sequence of numbers related to the number of implants within the cartridge, the tray-like portion forming two sides having aligned openings larger than the cross-sectional area of the implants, said tray-like portion including a plurality of detents spaced equally in a row a distance equal to the thickness of an implant, and said implant pusher including ratchet teeth to engage the detents for impeding the movement of the pusher.

10. An implant cartridge, comprising a generally rectangular container containing a series of elongated cylindrical implants in side-by-side relationship, a pusher movable against the series for moving the implants transversely of themselves to feed the same to an administration position, a corresponding row of detents on the container extending in the direction of movement, with the detents spaced from each other a distance equal to the thickness of an implant, the pusher having one or more teeth which engage the detents and impede the advancement of the pusher at intervals of movement corresponding to the thickness of an implant, and manually operable means for moving the pusher to successive positions of impediment for feeding the implants successively to the administration position.

11. An implant cartridge for supplying a series of cylindrical implants to an implanter, comprising a generally rectangular container having bottom and side walls and an end wall for containing a series of cylindrical implants in side-by-side relation between the side walls and parallel with the end wall, a top wall for retaining the implants in the containers, a pusher for moving the implants successively against the end wall, said side walls having openings adjacent the end wall in alignment with an implant positioned against said end wall and of sufficient size to pass such implant and a rod-like plunger advanced against the implant to move it lengthwise out of the cartridge, said top wall having an inwardly open slot interconnected with said openings in the side walls to clear a web on such plunger, and manually removable tab means detachably fixed to said cartridge and including end tabs for normally closing said side wall openings and a panel connected between said end tabs for normally closing said slot, so as to retain the implants and protect them from contamination.

12. A cartridge as in claim 11 in combination with an implanter comprising a body defining a central bore and an elongated slot opening upward from the bore, said body also having a side opening for the reception of the cartridge in a position in which an implant lying against the end wall of the cartridge is aligned with said bore and said slot connecting the cartridge side openings is disposed to open upward to said elongated body slot, and a plunger in said implanter and comprising an elongated rod movable axially of said bore to carry the implant from against said cartridge end wall out of the cartridge, said plunger having an operating portion connected to the rod by a web which rides in said elongated body slot, the cartridge slot being adapted to clear such web for movement across at least part of the width of the cartridge.

* * * * *